United States Patent

Cionni

[11] Patent Number: 5,843,184
[45] Date of Patent: Dec. 1, 1998

[54] ENDOCAPSULAR TENSION RING AND METHOD OF IMPLANTING SAME

[76] Inventor: Robert J. Cionni, 11425 Grandstone La., Cincinnati, Ohio 45249

[21] Appl. No.: 12,877

[22] Filed: Jan. 26, 1998

[51] Int. Cl.[6] ................................. A61F 2/14; A61F 2/16
[52] U.S. Cl. ...................................... 623/4; 623/5
[58] Field of Search ............................. 623/4–6

[56] References Cited

U.S. PATENT DOCUMENTS

| | | | |
|---|---|---|---|
| Re. 33,039 | 8/1989 | Arntt ........................................... | 623/6 |
| Re. 34,998 | 7/1995 | Langerman ................................. | 623/6 |
| 4,363,143 | 12/1982 | Callahan ..................................... | 623/6 |
| 4,494,254 | 1/1985 | Lopez ......................................... | 623/6 |
| 4,711,638 | 12/1987 | Lindstrom .................................. | 623/6 |
| 4,725,276 | 2/1988 | Bissonette et al. .......................... | 623/6 |
| 5,133,750 | 7/1992 | Momose et al. ............................. | 623/6 |
| 5,275,624 | 1/1994 | Hara et al. .................................. | 623/6 |
| 5,366,501 | 11/1994 | Langerman ................................. | 623/6 |
| 5,593,436 | 1/1997 | Langerman ................................. | 623/4 |
| 5,628,795 | 5/1997 | Langerman ................................. | 623/6 |
| 5,628,797 | 5/1997 | Richer ........................................ | 623/6 |
| 5,628,798 | 5/1997 | Eggleston et al. .......................... | 623/6 |
| 5,697,973 | 12/1997 | Peyman et al. ............................. | 623/6 |
| 5,766,244 | 6/1998 | Binder ........................................ | 623/6 |

OTHER PUBLICATIONS

Morcher GmbH, *Morcher IOL Optical precision in perfection, Capsule tension ring*, Undated, 1 page.

*Primary Examiner*—Mary Beth Jones
*Attorney, Agent, or Firm*—Wood, Herron & Evans, LLP

[57] ABSTRACT

An improved endocapsular tension ring and method of implanting same in a capsular bag of a human eye. The improved endocapsular tension ring is particularly adapted to provide long-term stabilization and centralization of the capsular bag during and after intraocular surgery in patients having missing or damaged zonules. In one aspect of the invention, the improved endocapsular tension ring includes an open-ended loop formed of biocompatible material that is constructed to be resilient to compression in the radial direction within the capsular bag to prevent shrinkage of the capsular bag during and after intraocular surgery. The improved endocapsular tension ring includes a fixation element joined to the open-ended loop that is adapted to be attached to the scleral wall of the eye and thereby stabilize and centralize the capsular bag within the posterior chamber of the eye without passing sutures through the capsular bag. Methods for implanting the improved endocapsular tension ring in the capsular bag of a human eye are also disclosed.

29 Claims, 3 Drawing Sheets

ENDOCAPSULAR TENSION RING AND METHOD OF IMPLANTING SAME

FIELD OF THE INVENTION

The present invention relates generally to eye implants for human eyes and, more particularly, to a capsular bag implant for stabilizing the capsular bag of a human eye during and after intraocular surgery.

BACKGROUND OF THE INVENTION

The human eye is susceptible to various diseases and abnormalities that can lead to impaired vision in the eye. In severe cases of ocular disease or abnormality, near or total loss of functional vision may result which can only be restored through intraocular surgery. For example, cataracts are caused by a gradual clouding of the lens and its surrounding material which, over an extended period, may result in complete loss of functional sight in the cataractous eye.

Intracapsular cataract extraction includes complete removal of the lens, the capsular bag enveloping the lens, and the zonules connecting the capsular bag to the scleral wall of the eye. Following their removal, an artificial intraocular lens (IOL) is then implanted in the anterior chamber of the eye, with the haptics of the IOL being received in the anterior chamber angle region between the iris and the cornea. Alternatively, the IOL can be sutured to the iris or scleral wall in the posterior chamber, with the haptics of the IOL resting between the iris and the ciliary body.

Extracapsular cataract extraction is performed to remove the cataractous lens while leaving the capsular bag and zonules intact within the posterior chamber of the eye. In this procedure, a capsulorhexis incision is performed to remove a generally circular mid-portion of the anterior capsule of the capsular bag, thereby leaving the posterior capsule, an annular anterior capsular flap and a generally circular anterior capsulorhexis edge. The cataractous lens is removed from the residual capsular bag and replaced with an artificial IOL. The IOL has haptics to engage an inner peripheral surface of the residual capsular bag and centralize the IOL within the capsular bag.

Those skilled in the art of ophthalmic surgical procedures will appreciate that the capsular bag is a delicate elastic membrane that envelops the lens. The capsular bag is connected to the scleral wall of the eye through zonule fibers that function to centralize the lens behind the iris and in alignment with the pupil. In eye patients with missing or damaged zonules from trauma or disease, the position of the capsular bag within the posterior chamber of the eye is unstable, making removal of the enclosed cataractous lens difficult and implantation of the IOL challenging.

In the past, capsular bag implants have been developed to stabilize the capsular bag during the extracapsular cataract extraction procedure and to generally centralize the capsular bag within the posterior chamber of the eye in patients having limited damaged or missing zonules. One known capsular bag implant, commercially available from Morcher GmbH of Stuttgart, Germany, under model designations Type 14, 14A and 14C, has been found to be successful in preventing shrinkage of the elastic capsular bag during the cataract extraction procedure and to improve stabilization of the intraocular environment in some patients with limited zonular dialysis or zonular weakness.

The Morcher capsular bag implant (endocapsular tension ring) comprises an open-ended loop of polymethyl methacrylate (PMMA) which is resilient to compression in the radial direction within the capsular bag. The Morcher capsular bag implant is adapted to be implanted in the residual capsular bag before or after the cataractous lens is removed, and to engage the inner peripheral surface of the residual capsular bag to prevent shrinkage. The general circular expansion of the capsular bag as provided by the Morcher capsular bag implant improves stabilization of the intraocular environment and lens centration during intraocular surgery in patients with limited zonular dialysis or generalized zonular weakness. The Morcher capsular bag implant may be sutured to the scleral wall of the eye by passing a loop around the endocapsular tension ring and then passing the suture through the annular anterior capsulorhexis flap or the peripheral edge of the capsular bag. However, passing a suture through the residual capsular bag jeopardizes the residual capsular bag's integrity and therefore jeopardizes long-term IOL centration and stabilization.

Notwithstanding the advancements made in the prior art in the field of capsular bag implants, there is a need for a capsular bag implant which improves stabilization of the intraocular environment during and after intraocular surgery. There is also a need for an improved capsular bag implant that provides long-term intraocular lens centration and stabilization in patients having more significant zonular dialysis or generalized progressive zonular weakness.

SUMMARY OF THE INVENTION

To these ends, the present invention sets forth an improved endocapsular tension ring and method of implanting same which is particularly adapted to provide long-term stabilization and centralization of the capsular bag in patients during and after intraocular surgery.

In one embodiment of the invention, the improved endocapsular tension ring includes an open-ended loop formed of biocompatible material. The open-ended loop is constructed to be resilient to compression in the radial direction within the capsular bag to prevent shrinkage of the capsular bag during and after intraocular surgery. A novel aspect of the invention includes a fixation element having one end fixed to the open-ended loop and a free end which preferably terminates in an eyelet. The eyelet of the fixation element is operable to receive a suture for attachment of the fixation element to the scleral wall of the eye and thereby stabilize and centralize the capsular bag within the posterior chamber of the eye.

The open-ended loop of the improved endocapsular tension ring generally lies in a plane, and the fixation element preferably extends from the loop outside of the plane. In one aspect of the invention, the fixation element is curved from the fixed end to the free end, and includes a portion that lies in a second plane offset from and generally parallel to the plane defined by the open-ended loop. The fixation element has one portion that extends from the fixed end inwardly from the loop. A second portion of the fixation element extends from the first portion outwardly toward the loop to define a curved "hook" or haptic member between the fixed end and the free end. Preferably, the fixation element lies within the circumference of the open-end loop.

During an extracapsular cataract extraction, the improved endocapsular tension ring is implanted in the capsular bag with its fixed end joined to the loop within the capsular bag, and its free end extending past the capsulorhexis edge and positioned anterior to the annular anterior capsular flap. A suture is passed through the eyelet of the fixation element and sutured to the scleral wall of the eye anterior to the capsular bag and posterior to the iris. The placement of the suture is chosen preferably near the location of the missing or damaged zonules to reduce or eliminate shifting of the capsular bag within the posterior chamber of the eye. Positioning of the eyelet anterior to the annular anterior capsular flap eliminates the need to pass a suture through the fragile capsular bag which, over time, might jeopardize or disrupt the integrity of the capsular bag. The improved endocapsular tension ring prevents shrinkage of the capsular bag and stabilizes and centralizes the implanted IOL in alignment with the pupil.

The above features and advantages of the present invention will be better understood with reference to the accompanying figures and detailed description.

BRIEF DESCRIPTION OF THE DRAWINGS

Reference will now be made to the accompanying figures from which the novel features and advantages of the present invention will be apparent.

DETAILED DESCRIPTION OF THE INVENTION

Figure 1:
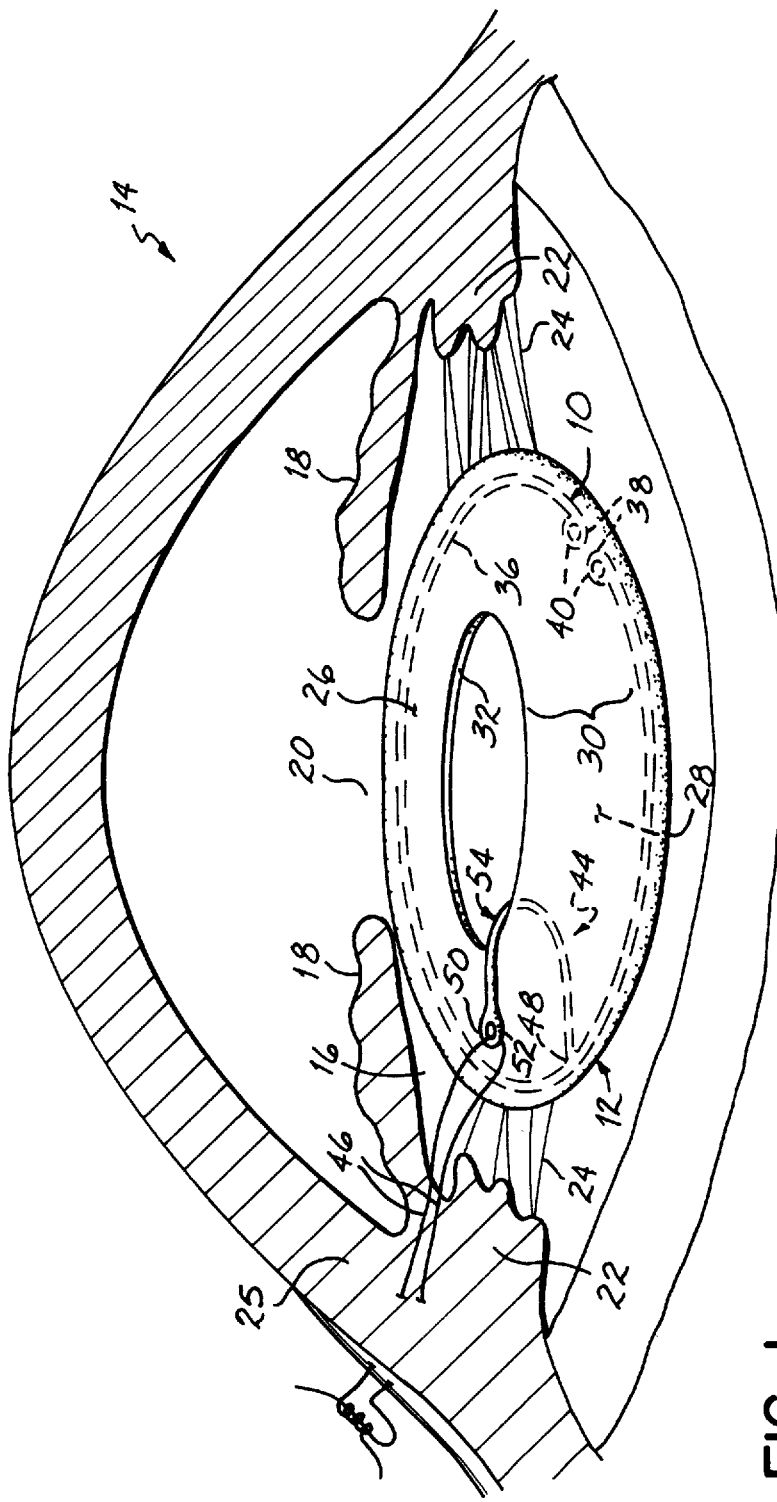
FIG. 1 is an illustration of a human eye, partially in cross-section, showing implantation of an improved endocapsular tension ring in a residual capsular bag in accordance with the principles of the present invention.

With reference to the figures, and to FIG. 1 in particular, an improved endocapsular tension ring 10 in accordance with one embodiment of the present invention is shown implanted in a capsular bag 12 of a human eye 14. As will be described in more detail below, the improved endocapsular tension ring 10 of the present invention is particularly adapted to stabilize and centralize the capsular bag 12 within the posterior chamber 16 of the eye 14 during and after intraocular surgery, particularly in patients that suffer from missing or damaged zonules from trauma or disease (zonular dialysis or weakness) or lens decentration.

In a normal human eye, the lens of the eye (not shown) is enveloped in the capsular bag 12 which is positioned centrally in the posterior chamber 16 of the eye behind the iris 18 and aligned with the pupil 20. The capsular bag 12 is an elastic membrane or pouch having a generally circular cross-section taken along a horizontal plane, and is attached to the ciliary body 22 of the eye through a series of zonules 24. The ciliary body 22 is attached to the scleral wall 25 of the eye. The zonules 24 are thin fibers that function to centralize the capsular bag 12 and its enveloped lens in a normal anatomic position within the posterior chamber 16 of the eye.

In patients suffering from missing or damaged zonules 24 from trauma or disease, as illustrated by the fewer zonules 24 on the left side of the capsular bag 12 shown in FIG. 1, the normal anatomic position of the capsular bag 12 may become unstable or decentralized in the posterior chamber 16 of the eye. The weakened or missing zonules 24 may allow the capsular bag 12 to shift or drift within the posterior chamber 16 of the eye, thereby resulting in general decentration of the lens and an unstable intraocular environment.

As shown in FIG. 1, the improved endocapsular tension ring 10 of the present invention is particulary adapted to be implanted in the capsular bag 12, and further to be attached to the scleral wall 25 of eye 14 for long-term stabilization of the capsular bag 12 in a normal anatomic position during and after intraocular surgery. The capsular bag 12 of FIG. 1 is illustrated as a residual capsular bag which remains following a capsulorhexis procedure commonly performed during intraocular surgery to remove a cataractous lens.

During the capsulorhexis surgical procedure, an incision is made in the anterior capsule 26 of the capsular bag 12 to remove a generally circular mid-portion of the anterior capsule 26. Following this procedure, the residual capsular bag 12 includes a posterior capsule 28, an annular anterior capsular flap 30, and a generally circular capsulorhexis edge 32 as shown most clearly in FIG. 1. As described in detail below, the residual capsular bag 12 is able to retain the improved endocapsular tension ring 10 and an artificial intraocular lens (IOL) 34 (FIG. 4) within the capsular bag 12 following the capsulorhexis procedure.

Referring now to FIGS. 1–4, the improved endocapsular tension ring 10 according to one embodiment of the present invention includes an open-ended loop 36 of biocompatible material having spaced ends 38, 38 terminating in respective eyelets 40, 40. The open-ended loop 36 is adapted to be implanted in the residual capsular bag 12 of eye 14 to prevent shrinkage of the capsular bag 12 during and after intraocular surgery.

More particularly, the open-ended loop 36 is implanted between the posterior capsule 28 and the annular anterior capsular flap 30 to engage an inner peripheral surface 42 (FIGS. 1 and 4) of the capsular bag 12 and to maintain a predetermined diameter of the capsular bag 12. The open-ended loop 36 is generally flexible to resist compression in a radial direction within the capsular bag 12. Preferably, the open-ended loop 36 has an unflexed diameter (not shown) of about 12 mm and a radially inward flexed diameter (FIG. 2) of about 10 mm, although other diameters of open-ended loops 36 are possible without departing from the spirit or scope of the present invention. The open-ended loop 36 is preferably made of polymethyl methacrylate (PMMA), although those skilled in the art will appreciate that other biocompatible materials suitable for implantation in a capsular bag 12 are also available.

The open-ended loop 36 further includes at least one fixation element 44 joined to the loop 36 which is adapted to be attached to the scleral wall 25 of eye 14 through a suture 46 (FIG. 1). The fixation element 44, also preferably made of PMMA or other suitable biocompatible material, has one end 48 integrally formed or fixed to the open-ended loop 36 and a free end 50 terminating in an eyelet 52 for receiving the suture 46 during attachment of the fixation element 44 to the scleral wall 25.

Figure 2:
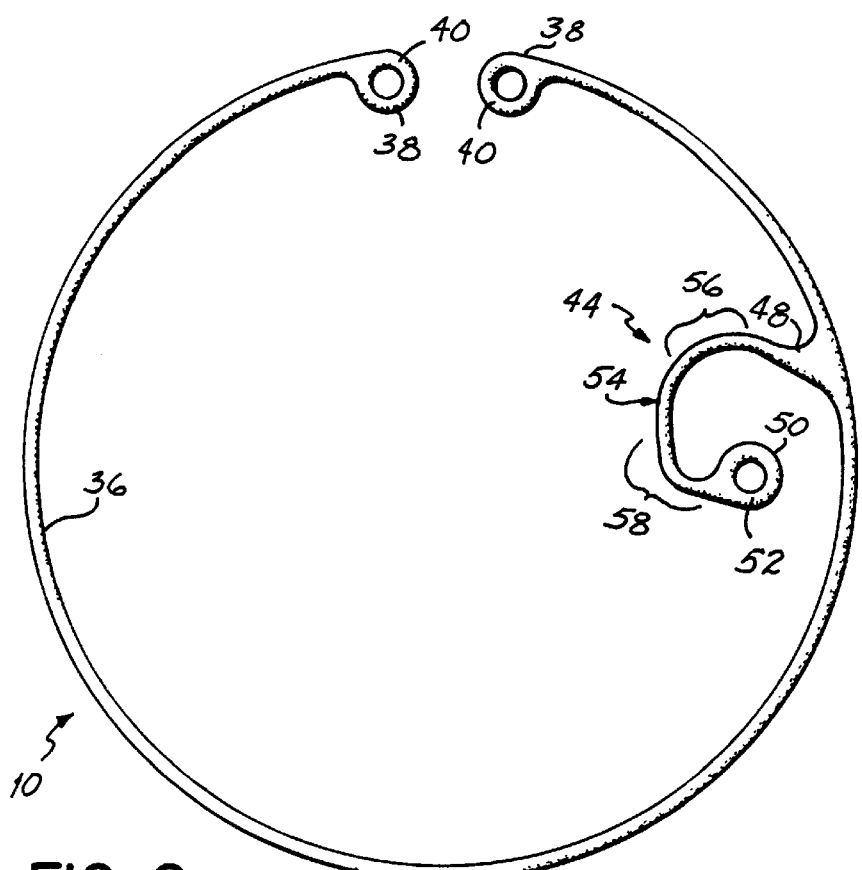
FIG. 2 is a top plan view of the improved endocapsular tension ring shown in FIG. 1.
Figure 3:
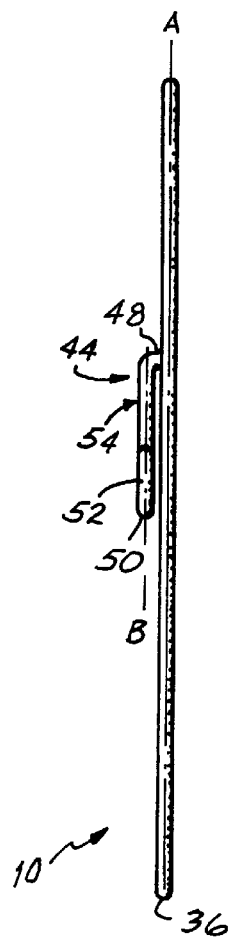
FIG. 3 is a side view of the improved endocapsular tension ring shown in FIG. 2.

As shown most clearly in FIG. 3, the open-ended loop 36 lies in a plane "A", while the fixation element 44 extends from the loop 36 outside of the plane "A". Preferably, as shown most clearly in FIG. 3, the fixation element 44 has a portion 54 lying in a second plane "B" offset from and generally parallel to plane "A" of the open-ended loop 36 for purposes to be discussed in more detail below. Fixation element 44 preferably has a first portion 56 extending from the fixed end 48 inwardly from the loop 36, and a second portion 58 extending from the first portion 56 outwardly toward the loop 36 to form a curved "hook" or haptic member between the fixed end 48 and the free end 50. As shown in FIG. 2, the fixation element 44 preferably lies within the circumference of the open-ended loop 36.

Figure 5:
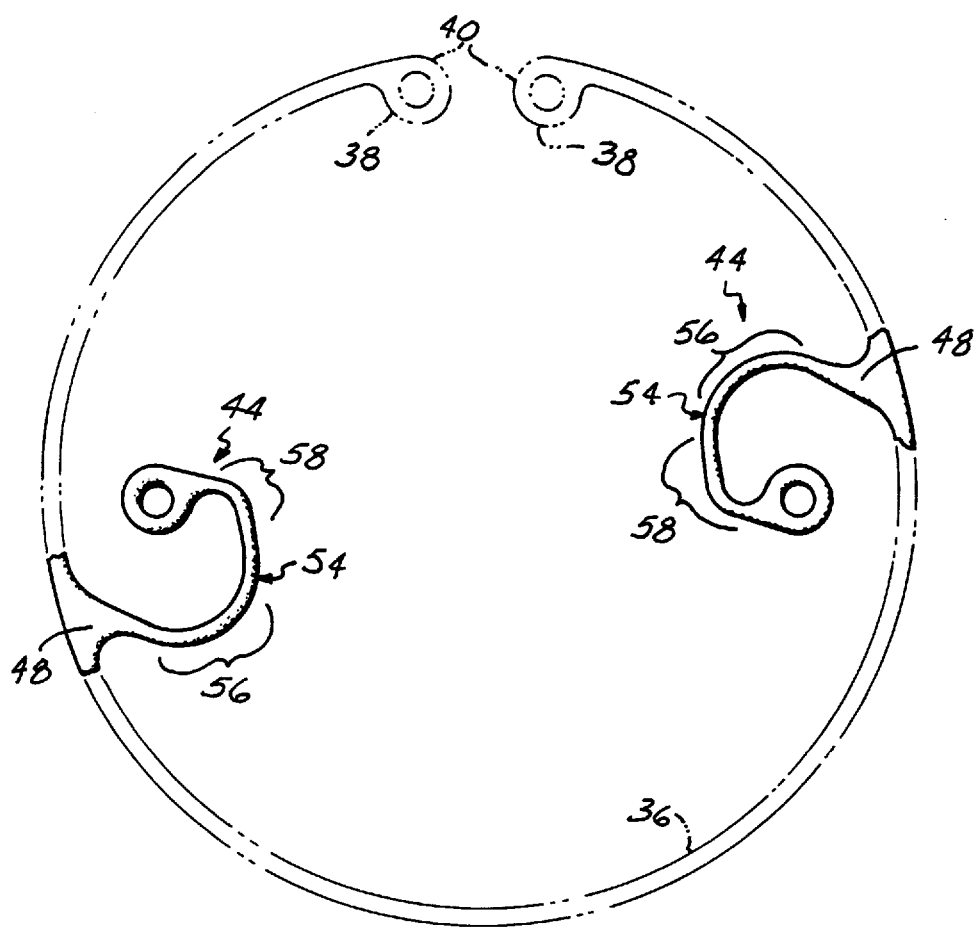
FIG. 5 is an alternative embodiment of the improved endocapsular tension ring shown in FIG. 2.

Aternatively, as shown in FIG. 5, the improved endocapsular tension ring 10 may include a pair of fixation elements 44 spaced on the open-ended loop 36 about 180° apart for attaching the improved endocapsular tension ring 10 to the scleral wall 25 of eye 14 at a pair of locations. The embodiment of the improved endocapsular tension ring 10 illustrated in FIG. 5 is particularly useful in cases of severe zonular damage or zonular weakness where more than one attachment point of the improved endocapsular tension ring 10 to the scleral wall 25 is required to stabilize and centralize the capsular bag 12 in the posterior chamber 16.

During intraocular surgery to remove a cataractous lens or to correct IOL lens centration, and in accordance with a preferred implantation method of the present invention, a capsulorhexis procedure is first performed to form the residual capsular bag 12 having the posterior capsule 28, annular anterior capsular flap 30 and capsulorhexis edge 32. A 10.0 PROLENE® suture 46 and needle (not shown) are thread through the eyelet 52 of fixation element 44 prior to implantation, and the needle and suture 46 are then passed through the scleral wall 25 anterior to the capsulorhexis edge 32 and posterior to the iris 18. It will be appreciated that other suture diameters and materials are possible without departing from the spirit or scope of the present invention.

Figure 4:
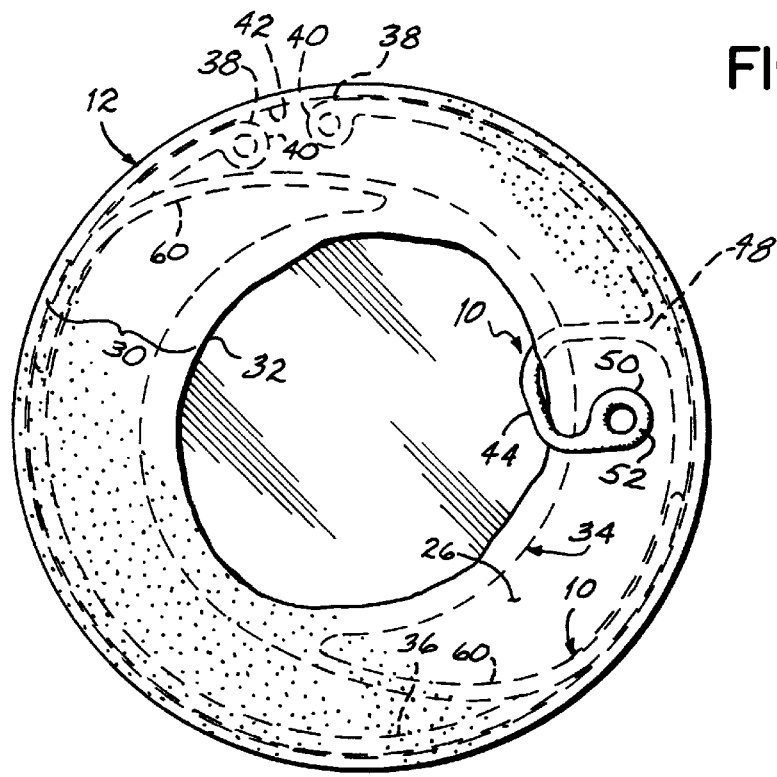
FIG. 4 is a fragmentary top view of a residual capsular bag following a capsulohexis procedure, showing implantation of the improved endocapsular tension ring of the present invention and an artificial intraocular lens in the capsular bag.

The improved endocapsular tension ring 10 is implanted in the residual capsular bag 12 of eye 14 between the posterior capsule 28 and the annular anterior capsular flap 30. The open-ended loop 36 is operable to generally prevent shrinkage of the capsular bag 12 as the loop 36 engages the inner peripheral surface 42 of the capsular bag 12. The fixation element 44 is positioned having its fixed end 48 joined to the loop 36 within the capsular bag 12, and its free end 50 extending past the capsulorhexis edge 32 and positioned anterior to the annular anterior capsular flap 30 and posterior to the iris 18. The suture 46 through eyelet 52 of fixation element 44 is sutured to the scleral wall 25 to thereby stabilize and centralize the capsular bag 12 in the posterior chamber 16 of the eye 14 during and after intraocular surgery. The placement of the suture 46 is chosen preferably near the location of the missing or damaged zonules to reduce or eliminate shifting of the capsular bag within the posterior chamber 16 of eye 14.

Where the natural lens (not shown) is to be replaced by an IOL, the IOL 34 shown in FIG. 4 is implanted in the capsular bag 12 which is stabilized by the improved endocapsular tension ring 10. The IOL 34 typically includes haptic members 60 which engage the inner peripheral surface 42 of the capsular bag 12.

Those skilled in the art will readily appreciate that the improved endocapsular tension ring 10 of the present invention advantageously prevents shrinkage of the capsular bag 12 during and after intraocular surgery. The fixation element 44 that is joined to the open-ended loop 36 and attached to the scleral wall 25 of eye 14 provides long-term stabilization and centralization of the capsular bag 12 during and after intraocular surgery in patients having missing or damaged zonules through zonular dialysis or weakness. With the eyelet 52 of fixation element 44 positioned anterior to the capsular bag, the suture 46 may be attached to the scleral wall 25 without passing through the fragile capsular bag 12. Through attachment of the fixation element 44 to the scleral wall 25 of the eye, the improved endocapsular tension ring 10 of the present invention also provides improved IOL centration and stabilization in patients having pre-existing or future zonular dialysis or zonular weakness.

From the above disclosure of the general principles of the present invention and the preceding detailed description of preferred embodiments, those skilled in the art will readily comprehend the various modifications to which the present invention is susceptible. The invention in its broader aspects is therefore not limited to the specific details and illustrative example shown and described. Accordingly, departures may be made from such details without departing from the spirit or scope of Applicant's general inventive concept.

Having described the invention, I claim:

1. An improved endocapsular tension ring for implantation into a residual capsular bag of an eye following a capsulorhexis procedure, comprising:
    a loop formed of biocompatible material, said loop being operable to generally prevent shrinkage of the capsular bag following implantation therein; and
    an elongated fixation element associated with said loop and formed of biocompatible material, said fixation element having a first end fixed to said loop and a second free end adapted to be positioned anterior to the capsular bag, said fixation element being operable to receive a suture for attachment to the scleral wall of the eye without passing the suture through a wall of the capsular bag, whereby said endocapsular tension ring generally stabilizes and centralizes the capsular bag in the posterior chamber of the eye during and after intraocular surgery following attachment of said fixation element to the scleral wall.

2. The improved endocapsular tension ring of claim 1 wherein said loop lies in a plane and said fixation element extends from said loop outside of the plane.

3. The improved endocapsular tension ring of claim 1 wherein said loop lies in a first plane and said fixation element has a portion lying in a second plane generally parallel to the first plane.

4. The improved endocapsular tension ring of claim 1 wherein the second free end of said fixation element includes an eyelet for receiving the suture during attachment of said fixation element to the scleral wall of the eye.

5. The improved endocapsular tension ring of claim 1 wherein said fixation element is generally curved from the first fixed end to the second free end.

6. The improved endocapsular tension ring of claim 5 wherein the second free end of said fixation element lies within the circumference of said loop.

7. The improved endocapsular tension ring of claim 1 wherein said loop is made of polymetheylmethacrylate.

8. The improved endocapsular tension ring of claim 1 wherein said fixation element is made of polymetheylmethacrylate.

9. An improved endocapsular tension ring for implantation into a residual capsular bag of an eye following a capsulorhexis procedure, the residual capsular bag having a posterior capsule, an annular anterior capsular flap and an anterior capsulorhexis edge, comprising:
    a loop of biocompatible material, said loop being operable to generally prevent shrinkage of the capsular bag following implantation therein between the posterior capsule and the annular anterior capsular flap; and
    an elongated fixation element joined to said loop and formed of biocompatible material, said fixation element having a first end fixed to said loop and a second free end adapted to extend past the anterior capsulorhexis edge and adapted to be positioned anterior to the capsular bag, the second free end of said fixation element being operable to receive a suture for attachment to the scleral wall of the eye without passing the suture through a wall of the capsular bag, whereby said endocapsular tension ring generally stabilizes and centralizes the capsular bag in the posterior chamber of the eye during and after intraocular surgery following attachment of said fixation element to the scleral wall.

10. The improved endocapsular tension ring of claim 9 wherein the second free end of said fixation element includes an eyelet for receiving the suture during attachment of said fixation element to the scleral wall of the eye.

11. The improved endocapsular tension ring of claim 9 wherein said fixation element is generally curved from the first fixed end to the second free end.

12. The improved endocapsular tension ring of claim 9 comprising a pair of fixation elements, each of said fixation elements having a first end fixed to said loop and a second free end adapted to extend past the anterior capsulorhexis edge and adapted to be positioned anterior to the capsular bag, the second free end of each said fixation element being operable to receive a suture for attachment to the scleral wall of the eye without passing the suture through a wall of the capsular bag.

13. The improved endocapsular tension ring of claim 12 wherein said pair of fixation elements are spaced on said loop about 180° apart.

14. An improved endocapsular tension ring for implantation into a residual capsular bag of an eye following a capsulorhexis procedure, the residual capsular bag having a posterior capsule, an annular anterior capsular flap and an anterior capsulorhexis edge, comprising:

a loop of biocompatible material, said loop being operable to generally prevent shrinkage of the capsular bag following implantation therein between the posterior capsule and the annular anterior capsular flap; and a generally curved elongated fixation element joined to said loop and formed of biocompatible material, said fixation element having a first end fixed to said loop and a second free end adapted to extend past the anterior capsulorhexis edge and adapted to be positioned anterior to the capsular bag with the annular anterior capsular flap positioned therebetween, the second free end of said fixation element having an eyelet to receive a suture for attachment to the scleral wall of the eye without passing The suture through a wall of the capsular bag, whereby said endocapsular tension ring generally stabilizes and centralizes the capsular bag in the posterior chamber of the eye during and after intraocular surgery following attachment of said fixation element to the scleral wall.

15. The improved endocapsular tension ring of claim 14 wherein said fixation element is integrally formed with said loop.

16. The improved endocapsular tension ring of claim 14 wherein said fixation element is attached to said loop.

17. An improved endocapsular tension ring construction, comprising:

a generally flexible open-ended loop free of attachment to an intraocular lens, said loop having first and second ends, and a first elongated fixation element having a first portion projecting inwardly from said loop and a second portion extending outwardly from said first portion, said first fixation element being open-ended with one end fixed to said loop and the other end free.

18. The improved endocapsular tension ring of claim 17 wherein said the first and second portions of said fixation element are generally curved.

19. The improved endocapsular tension ring of claim 17 wherein said loop lies in a plane and said fixation element extends from said loop outside of the plane.

20. The improved endocapsular tension ring of claim 17 wherein said loop lies in a first plane and said fixation element has a portion lying in a second plane generally parallel to the first plane.

21. The improved endocapsular tension ring of claim 17 wherein each of the first and second ends of said loop includes an eyelet.

22. The improved endocapsular tension ring of claim 17 wherein the free end of said fixation element includes an eyelet.

23. The improved endocapsular ring construction of claim 22 further comprising a second fixation element projecting from said loop, said second fixation element being open-ended with one end fixed to said loop and the other end free.

24. The improved endocapsular ring construction of claim 23 wherein said first and second fixation elements are spaced on said loop about 180° apart.

25. A method of implanting an endocapsular tension ring in a capsular bag of an eye, comprising:

providing a loop of biocompatible material, said loop being operable to generally prevent shrinkage of the capsular bag following implantation therein;

providing an elongated fixation element joined to said loop and formed of biocompatible material, said fixation element having a first end fixed to said loop and a second free end;

removing a mid-portion of the anterior capsule of the capsular bag, thereby leaving the posterior capsule, an annular anterior capsular flap and an anterior capsulorhexis edge;

implanting said loop in the capsular bag between the posterior capsule and the annular anterior capsular flap;

positioning said fixation element having its first end fixed to said loop and its second free end extending past the capsulorhexis edge and positioned anterior to the capsular bag with the annular anterior capsular flap positioned therebetween; and attaching the second free end of the fixation element to the scleral wall of the eye, whereby said endocapsular tension ring generally stabilizes and centralizes the capsular bag in the posterior chamber of the eye during and after intraocular surgery following attachment of said fixation element to the scleral wall.

26. The method of claim 25 further comprising positioning the second free end of the fixation element posterior to the iris of the eye.

27. The method of claim 25 wherein the attaching step comprises suturing the second free end of said fixation element to the scleral wall of the eye.

28. The method of claim 27 wherein the attaching step further comprises positioning the suture anterior to the annular anterior capsular flap and posterior to the iris of the eye.

29. A method of implanting an endocapsular tension ring in a capsular bag of an eye, comprising:

providing a loop of biocompatible material, said loop being operable to generally prevent shrinkage of the capsular bag following implantation therein;

providing a generally curved fixation element joined to said loop and formed of biocompatible material, said fixation element having a first end fixed to said loop and a second free end terminating in an eyelet;

removing a mid-portion of the anterior capsule of the capsular bag, thereby leaving the posterior capsule, an annular anterior capsular flap and an anterior capsulorhexis edge;

implanting said loop in the capsular bag between the posterior capsule and the annular anterior capsular flap;

positioning said fixation element having its first end fixed to said loop and its second free end extending past the capsulorhexis edge positioned anterior to the capsular bag with the annular anterior capsular flap positioned therebetween; and suturing the eyelet on the second free end of the fixation element to the scleral wall of the eye, whereby said endocapsular tension ring generally stabilizes and centralizes the capsular bag in the posterior chamber of the eye during and after intraocular surgery following attachment of said fixation element to the scleral wall.

* * * * *